US005562616A

United States Patent [19]

Haber et al.

[11] Patent Number: 5,562,616

[45] Date of Patent: Oct. 8, 1996

[54] SEMI-AUTOMATIC RECONSTITUTING SYSTEM FOR BINARY ONCOLYTIC PHARMACEUTICALS

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Lake Forest, Calif.

[21] Appl. No.: 396,919

[22] Filed: Mar. 1, 1995

[51] Int. Cl.[6] .................... A61M 37/00

[52] U.S. Cl. .................... 604/82; 604/86; 604/191

[58] Field of Search .................... 604/82, 83, 85, 604/86, 87, 88, 89, 403, 408, 411–416, 905, 201, 200, 205, 206, 218, 191

[56] References Cited

U.S. PATENT DOCUMENTS 3,923,059 12/1975 Ogle .
4,505,709 3/1985 Froning .
4,713,062 12/1987 Stevanato .
5,067,948 11/1991 Haber .
5,158,546 10/1992 Haber .
5,304,165 4/1994 Haber .
5,364,386 11/1994 Fukuoka et al. .................... 604/411
5,385,546 1/1995 Kriesel et al. .................... 604/411
5,397,303 3/1995 Sancoff et al. .................... 604/82
5,423,752 6/1995 Haber et al. .................... 604/86
5,478,337 12/1995 Okamoto et al. .................... 604/413

*Primary Examiner*—John D. Yasko
*Attorney, Agent, or Firm*—Townsend and Townsend and Crew

[57] ABSTRACT

A method and apparatus for preparing a binary liquid, highly toxic cancer treatment pharmaceutical for administration to a patient from an I.V. bag is disclosed. Liquid components of the pharmaceutical are furnished in septum-sealed vials which are mixed in a syringe structure formed by a body having a mixing chamber in fluid communication with first and second ports. The vials are attached to the body at the first port, their septum is pierced, and a normally closed valve between the first port and the chamber is opened so that the liquid components flow along a sealed path into the chamber to prevent contact between the components and the surrounding environment. The I.V. bag is attached to the body at the second port and is pierced by a needle in response to movement of the bag towards the syringe body. This movement is used to open a valve between the second port and the chamber so that the mixed pharmaceutical can be flowed along a sealed path into the I.V. bag to prevent contact between the pharmaceutical and the environment until the transfer of the pharmaceutical to the bag has been completed. The syringe structure is inexpensive, can be injection molded, and is discarded after its use.

37 Claims, 2 Drawing Sheets

SEMI-AUTOMATIC RECONSTITUTING SYSTEM FOR BINARY ONCOLYTIC PHARMACEUTICALS

BACKGROUND OF THE INVENTION

The present invention relates to a method and a device for mixing highly toxic, corrosive, etc. substances, and in particular cancer treatment pharmaceuticals having such characteristics, and delivering the mixed substance; e.g. the pharmaceutical, to a receptacle such as an I.V. bag for subsequent administration of the pharmaceutical to a patient.

The use of certain toxic, tissue (e.g. skin) attacking pharmaceuticals for the treatment of cancer has expanded. For example, a group of compounds derived from the yew tree which grows in tropical rain forests and which, for example, are available under the trademark TAXOIDS (a trademark of Rhone-Poullange) has become more common. Typically, such pharmaceuticals are first prepared by mixing at least two (for binary systems) components and then delivering the mixed components to an I.V. bag for intravenous administration. In the body, the pharmaceutical disrupts the DNA of cancer cells and their reproductive cycle. The commercially available TAXOIDS pharmaceutical is prepared by mixing two liquid components delivered in septum-sealed vials, one vial containing the pharmaceutically active cancer treatment, and the other a diluent.

In the past, the mixing and delivery of the pharmaceutical was typically done with syringes which had to be inserted into and withdrawn from the vials and the I.V. bag. This is time-consuming task and spillage of toxic liquids could occur several times while the pharmaceutical was prepared and delivered to the I.V. bag.

The active compounds are so toxic that even a minor leak; e.g. a drop which may accidentally spill onto a person's skin, requires a skin graft to heal. Since the entire operation requires the passage of the pharmaceutical, and of its components, between multiple containers and receptacles and each such transfer has the potential of leakage, medical personnel preparing the pharmaceuticals have heretofore been exposed to significant danger from coming into skin contact with them.

Thus, there is presently a need for both simplifying the preparation and delivery of such toxic substances, including particularly the above-mentioned cancer treatment pharmaceuticals, and preventing contact between medical personnel preparing them.

SUMMARY OF THE INVENTION

In general terms, the present invention achieves this by providing a syringe structure with a mixing chamber for the components of the pharmaceutical and providing seals and valves at the points of connection for the vials and the I.V. bag, respectively, which are applied and sequentially opened and closed in a manner so that the transfer of liquids between the vials, the chamber and the I.V. bag takes place in an automatically activated, fully sealed and correspondingly safe environment.

In terms of the method, this is attained by sealing the flow paths between the vials, the I.V. bag and the mixing chamber before sequentially establishing flow communication between them. The vials are sequentially attached to a first port of the syringe structure, and the first and second components are then flowed into the chamber along sealed flow paths and mixed in the chamber to prepare the pharmaceutical. Fluid communication between the chamber and the port connected to the vial is then closed and the I.V. bag is fluidly connected to the chamber for the transfer of the pharmaceutical into the bag. Preferably, this is done by initially piercing a closed tubular port of the I.V. bag and in response thereto or thereafter opening a normally closed valve so that the pharmaceutical can be flowed from the chamber into the bag.

An important aspect of the present invention is that the opening and closing of the valves between the mixing chamber and the respective ports is effected by moving respective vial septum and I.V. port piercing needles longitudinally in opposite directions.

The apparatus of the present invention broadly includes a syringe structure which is preferably defined by a body that has a cylindrical mixing chamber cooperating with a reciprocating piston. Conduits formed in the syringe structure provide fluid communication between the chamber and first and second ports on the housing. The conduits are normally closed by a valve for each port. Each port has a holder for attaching containers to the syringe structure. Each holder has a linearly reciprocable member, such as a vial docking cage and an I.V. bag carrier, and an actuator operatively coupled to the member and the valve for opening the valve in response to movement of the member in a first direction, e.g. when a vial or an I.V. bag is first attached. The respective valves are closed again in response to movement of the member in a second direction opposite to the first direction. In this manner vials holding the pharmaceutical components can be sequentially connected to the first port for sequentially flowing the contents into the chamber and mixing therein. The I.V. bag is then connected to the second port for flowing the solution from the chamber into the bag.

In a preferred embodiment the vials are attached to the first port by constructing the associated holder in the form of a docking cage formed by a plurality of jaws which are resiliently mounted in the reciprocating member so that they surround the neck of the vial and position its septum at the member. A cannula is further attached to the member, and its sharp end extends past the member so that it pierces the septum as the vial neck is grasped by the jaws of the holding cage.

Once attached to the docking cage the vials with the member and the needle are moved towards the syringe structure, preferably with a closed safety cup placed over the vial, and threaded onto the syringe structure for both sealing the interior thereof, and therewith the contents of the vials from the environment, and opening the associated valve so that the contents of the vials can be sequentially drawn into and mixed in the mixing chamber of the syringe structure.

Another aspect of the invention contemplates to provide a threaded connection between the piston and the syringe body so that the piston is reciprocated in the chamber by manually turning a rotator. This is particularly useful for instances in which one or more of the components that must be mixed are highly viscous and require the application of significant axial forces to the piston.

A further important aspect of the present invention is that the entire device can be relatively inexpensively constructed so that it can be used as a throw-away device. This is achieved by providing a unitary body, injection molded, for example, from a translucent or transparent material which is resistant to the compounds it is being used with, such as a clear polypropylene or other thermoplastic polymers when used with the TAXOIDS pharmaceutical, for example, and which incorporates the mixing chamber, the ports for attachment of the vials and the I.V. bag, and the valves for establishing and preventing fluid communication therebetween. Simple and inexpensive helical compression springs are used to bias the vial holder and I.V. bag carrier into extended positions (away from the body) and which are designed so that the biasing force exerted by them is greater than the force required for piercing the septum and port of the vial and I.V. bag, respectively.

The cooperating piston and mixing chamber can be sized so that multiple doses of pharmaceutical components can be mixed before delivery to the I.V. bag. This is achieved by sequentially affixing two or more; e.g. three, sets of vial holding components at the first port of the syringe structure and sequentially flowing the contents of each vial into the chamber for mixing therein before the I.V. bag is attached to the second port for the transfer of the pharmaceutical into the bag. In this manner, pharmaceutical quantities which vary, for example, with the size of the patient can be mixed in one and the same mixing device of the present invention. This arrangement is facilitated by constructing the body for the syringe structure, at least in the area of the mixing chamber, of a transparent material, such as the earlier mentioned clear polypropylene, and applying a volumetric graduation scale to the body so that the user can see the quantity of components drawn into the chamber.

DESCRIPTION OF THE PREFERRED EMBODIMENTS

Figure 1:
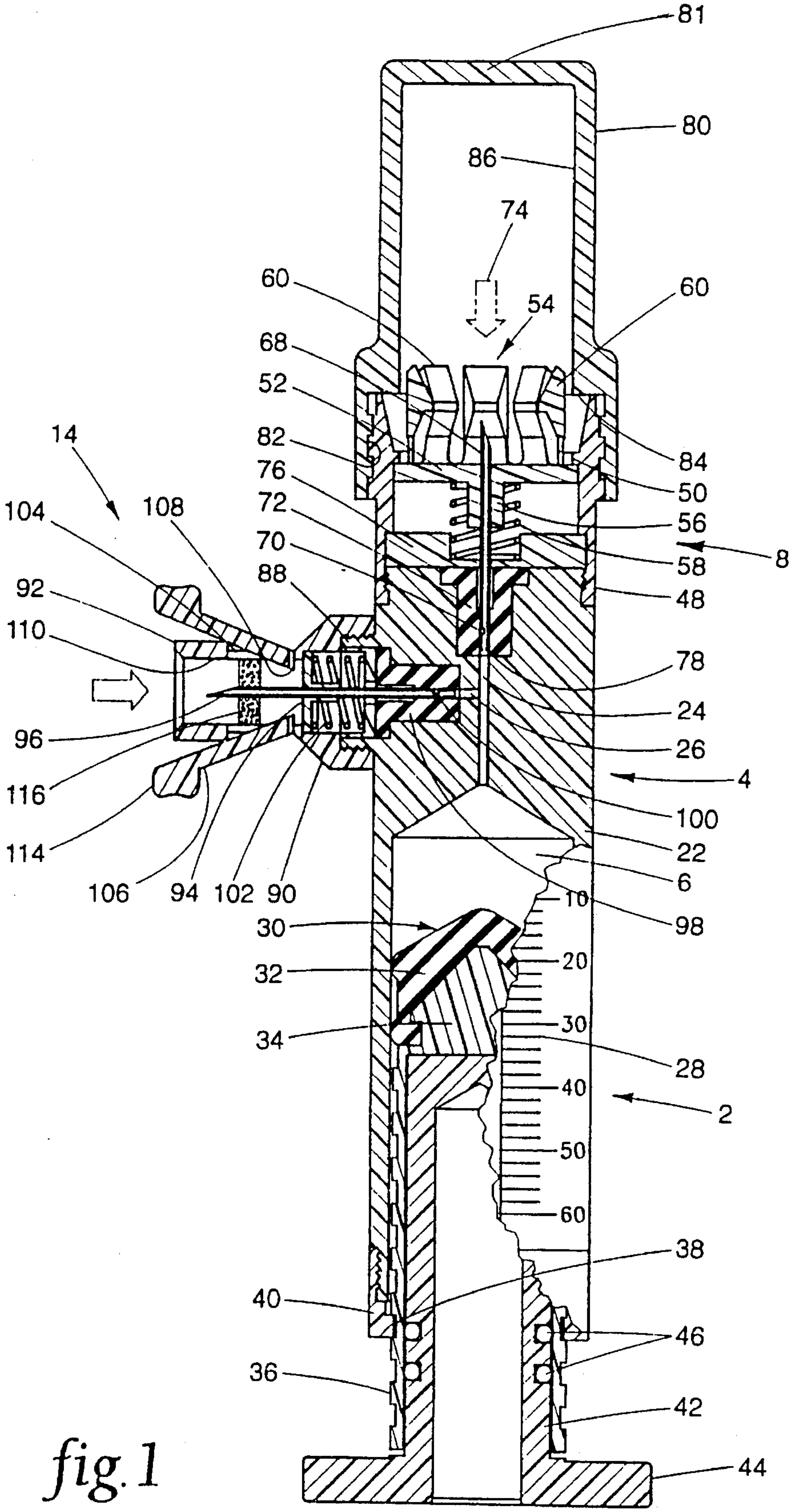
FIG. 1 is a side elevation, in section, through an apparatus constructed in accordance with the present invention for mixing a pharmaceutical from components in at least two vials and delivering the resulting pharmaceutical to an I.V. bag for administration to a patient.
Figure 2:
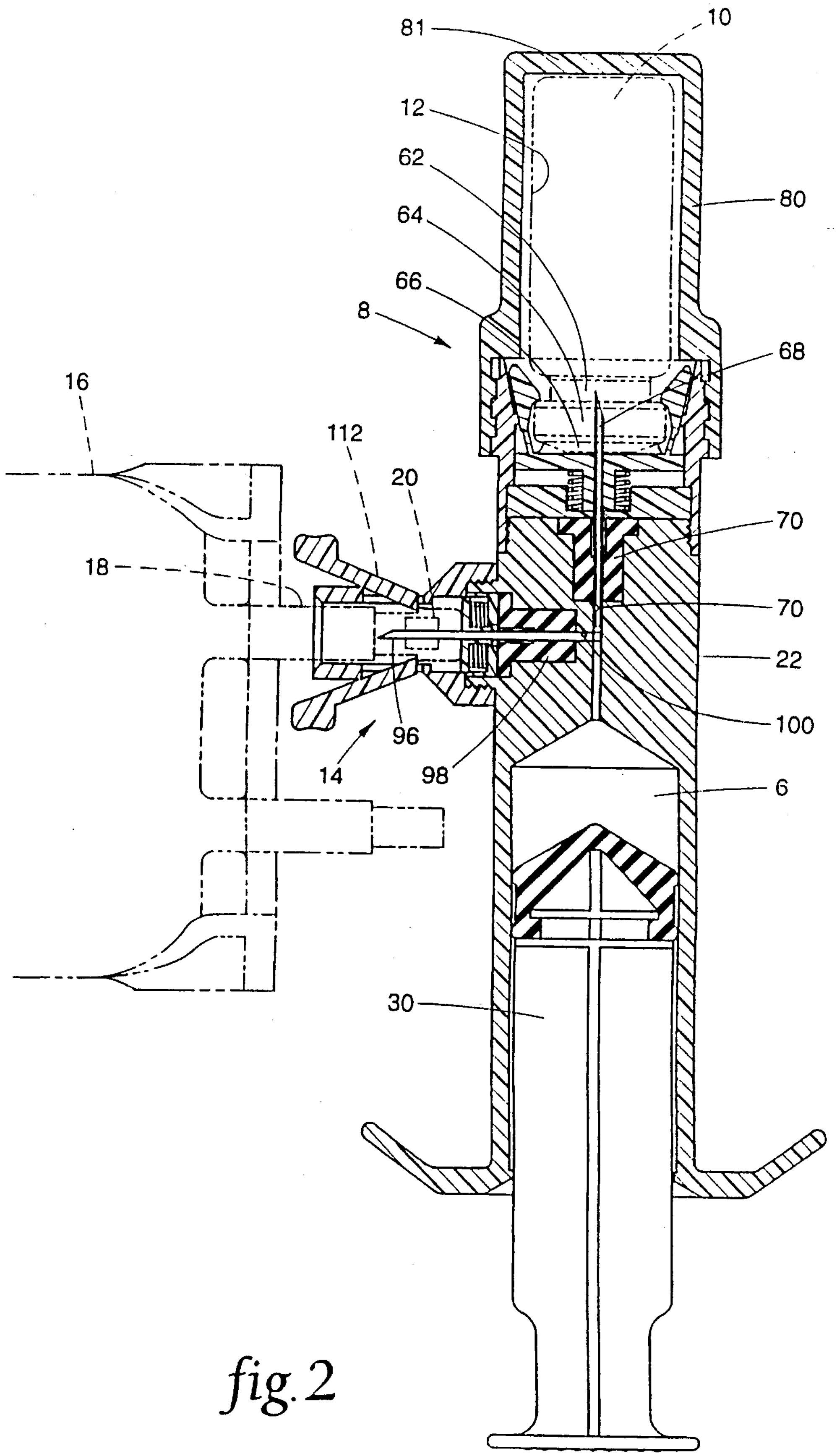
FIG. 2 is similar to FIG. 1, shows a vial and an I.V. bag attached to the device and in fluid communication with the mixing chamber, and is provided only to better illustrate the functioning of the device, although it should be noted that in actual use the vial and the I.V. bag will not be in simultaneous fluid communication with the mixing chamber.

Referring to FIGS. 1 and 2, a mixing and delivery device 2 constructed in accordance with the present invention for reconstituting a binary pharmaceutical, for example, is formed by a syringe structure 4 which includes a mixing chamber 6 and has a first port 8 at which vials 10 are positioned for transferring their contents to the mixing chamber. On their interiors 12 the vials hold the liquid components of the pharmaceutical that require mixing before use. The syringe structure includes a second port 14 to which a conventional I.V. bag 16 having a tubular port 18 closed at 20 is attached. After the pharmaceutical has been mixed in the chamber, it is transferred into the I.V. bag for subsequent intravenous administration.

The syringe structure is preferably formed by injection molding a cylindrical body 22 from clear polypropylene, for example, and forming therein a concentric, cylindrically shaped mixing chamber 6, an inner end of which is in fluid communication with the first and second ports 8, 14 via a concentric first and a laterally extending second cylindrical flow bore 24, 26 which merge at a point spaced from an interior end of the chamber. The exterior of the body may include a volumetric scale 28 for the chamber for observing the liquid volume therein.

A piston 30 extends past an open end of the chamber, is axially reciprocably movable in the chamber, and includes a sealing piston head 32 mounted at the end of a plunger 34 which carries external threads 36 engaging a corresponding internal thread 38 on the body; for example, on a ring fitting 40 threaded onto the end of the body. The plunger is cylindrically hollow and receives a rotator 42 with a knob or finger actuator 44 so that it can be rotated about its axis. One or more friction rings 46; for example, compressed elastomeric (e.g. rubber or plastic) 0-rings, are disposed in corresponding ring grooves on the portion of the rotator extending into the plunger to generate friction between the plunger and rotator so that rotation of the latter causes corresponding rotation of the former and thereby axially advances the piston into or retracts it from the mixing chamber. The frictional force generated by the friction rings can be selected so that a pre-set, maximum torque that can be transferred between the rotator and the plunger cannot be exceeded, to prevent possible damage to the device from excessive pressures in the mixing chamber and the flow bores, particularly when handling liquids having a relative viscosity such as the earlier mentioned TAXOIDS pharmaceutical.

If desired, a simple pull-push type piston (shown in FIG. 2) can be used instead of the rotatable piston described above.

Referring now primarily to the right-hand side of FIG. 1, first port 8 is at the end of cylindrical body 22 opposite from the open mixing chamber end and is externally threaded to receive a coaxial, generally tubular vial docking housing 48 which extends past the end of the body and includes an inwardly projecting nose 50 spaced a distance from the end of body 22. A movable disk 52 of a vial docking cage 54 is coaxial with the syringe body, includes a hub 56, and is reciprocable in an axial direction between an extended position, in which it engages nose 50 (shown in FIG. 1), and a retracted position, in which the disk is proximate the syringe body end (not shown in FIG. 1). A helical compression spring 58 biases the disk into its extended position.

The disk includes a plurality of circumferentially spaced-apart jaws 60 which are resiliently expandable in a radially outward direction, preferably by means of the resiliency of the material (e.g. plastic) of which they are constructed. The jaws are shaped to engage an undercut 62 of vial neck 64 forming an opening into the vial which is closed by a pierceable septum 66 constructed, for example, of an elastomeric material as is well known and widely practiced in the industry. The vial is manually pushed past the jaws until they snap back behind the neck of the vial to thereby also pierce the septum with a first needle cannula 68. When engaged, the jaws retain the end of the vial neck covered by the septum against the face of disk 52.

The first needle cannula 68 is press-fit or otherwise suitably attached to disk 52 and hub 56 so that the needle reciprocates with the hub. A first free end of the needle is pointed, for piercing the vial septum as described above. A second end of the needle is on the interior of the body when the disk is in its extended position, is closed, and includes a lateral orifice or cannula side eye 70 which communicates with the hollow interior of the needle. A tubular first valve 72 formed of an elastomeric material, such as latex or a thermoplastic rubber ("TPR"), is mounted in syringe body 22 concentrically with flow bore 24.

The tubular valve snugly engages the exterior of the inner needle end and covers the side eye 70 when disk 52 is in its extended position to thereby prevent fluid communication between the mixing chamber and the interior of the needle at the first port. When the disk is axially moved towards the body in the direction of arrow 74, needle 68 moves with it and before the end of such travel is reached by the disk; e.g. before its back side engages or bottoms out on a retaining plate 76 applied to the ends of the body, side eye or first orifice 70 is positioned past an inner end 78 of the tubular valve. Fluid communication between the needle interior and the mixing chamber via flow bore 24 is thereby established. The retaining plate 76 seats spring 58 and retains tubular valve 72 in the body.

A cylindrical safety cup 80 having an open end with an internal thread 82 is provided for placement over vials 10 attached to the docking cage at the first port 8. The other end 81 of the cup is closed. The internal thread of cup 80 cooperates with a corresponding external thread on the free end of vial docking housing 48 so that the cup can be threaded onto the docking housing until the end face of the housing engages an annular stop surface 84 of the cup as is illustrated in FIG. 1. The remainder of the cup interior is defined by a cylindrical wall 86 which is dimensioned so that the vial can be received therein.

The cup is dimensioned so that the closed end of the cup pushes against the vial attached to docking cage 54. Before the free end of the docking housing engages the stop surface, disk 52 and therewith needle 68 are linearly moved inwardly towards the mixing chamber a sufficient distance to free side eye 70 and establish fluid communication between the chamber and the interior of the vial. Further, jaws 60 become locked in a vial retaining position because the free ends of the jaws will have moved past the annular stop surface 84, at which point the cylindrical inner wall 86 of the cup prevents any substantial outward expansion of the jaws. These steps occur before the disk bottoms out.

To assure the desired sequence of motions, spring 58 is constructed so that the force with which it biases the disk against nose 50 exceeds the force required to dilate the jaws, or spread them radially outwardly, and the force required for the free needle end to penetrate the septum. Thereafter, the continued turning of the cup to thread it onto the docking housing will overcome the biasing force so that the disk and therewith the needle begin to move inwardly towards the mixing chamber to open the first valve.

Once the free end of docking housing 48 has bottomed out against stop surface 84, piston 30 is retracted to aspirate the liquid component from the attached vial via needle 68, side eye 70 and flow bore 24 into the mixing chamber. When the contents of the vial have been withdrawn from it, safety cup 80 is unscrewed from the docking housing. Spring 58 thereby returns disk 52 and needle 68 to their extended position to close the first valve and prevent fluid from flowing from the mixing chamber to the free needle end even before the pointed needle end is fully withdrawn from the vial and its septum. Thereafter, the empty vial is removed from the docking cage 54 and a vial containing the second component for the pharmaceutical is attached to the first port in the above-described manner so that, upon the aspiration of the contents of the second vial, the pharmaceutical (assuming a binary system) becomes mixed in the mixing chamber. If additional quantities of pharmaceutical are required, the contents of additional vial sets holding the components for the pharmaceutical are transferred into the mixing chamber by repeating the just-described procedure.

The second port 88 of the mixing-delivery device 2 of the present invention is preferably defined by a threaded nipple 88 which protrudes laterally from syringe body 22 and receives a tubular end fitting 90 terminating in a free, open tubular end 92. A needle carrier 94 including a disk facing the open end of the fitting is aligned with second flow bore 26 and linearly reciprocable between positions remote from (shown in FIG. 1) and proximate to (not shown in FIG. 1) the body 22. An undercut in the end fitting limits movement of the carrier beyond the remote position. The carrier mounts a second needle cannula 96 having a free end for piercing the seal 20 in I.V. bag port 18. An inner end of the second needle is concentric to the second flow bore, extends into the syringe body, and is surrounded by a second tubular elastomeric valve 98 mounted in the syringe body. When the carrier is in its extended or remote position, the second tubular valve covers a second side eye or orifice 100 to normally prevent fluid communication between the mixing chamber 6 and the interior of the second needle. As with the first needle, the inner end of the second needle is closed.

A second helical compression spring 102 is disposed between a retaining plate or cup 104 and the underside of the needle carrier to bias the latter into its remote position. The retaining plate centers one end of the spring and retains the second valve in its position in body 22.

In a presently preferred embodiment, end fitting 90 includes a pair of oppositely disposed, longitudinally extending slots 104 through which a pair of latches 106 extend. The latches are hingeable relative to the end fitting and include inner ends 108 which extend into a tubular passage 110 defined by the end fitting and sized to slidably receive the tubular port 18 of the I.V. bag. The inner ends 108 of the latches are dimensioned so that they engage an undercut 112 of the I.V. bag port when it is fully inserted in the tubular passage. When in this position a free end of the tubular I.V. bag port has forced the needle carrier a sufficient distance towards the syringe body to move second side eye 100 of the second needle 96 past the inner end of the second tubular valve 98. This establishes fluid communication between the mixing chamber and the interior of the second needle.

There are a variety of ways for pivotally securing the latches to longitudinal slots 104 in end fitting 90. The latches can be injection molded with end fitting 90 and a molded, flexible hinge can be provided. The latches can also be pivotally retained to the fitting and in the slots by applying a band surrounding the exterior of the latches and of the end fitting.

The compression spring biasing the needle carrier into its remote position is constructed so that the following occurs in sequence as the I.V. bag port is slidably inserted into the tubular passage 110. The free needle end initially pierces through I.V. bag seal 20 as the tubular port is advanced towards the syringe body. Only thereafter the biasing force exerted by spring 102 can be overcome to commence movement of the needle carrier and the needle attached thereto towards the syringe body. The needle carrier, the needle, the second side eye 100, and the second valve are arranged relative to the location of undercut 112 on the I.V. bag port so that the second side eye clears the inner end of the second valve 98 and the inner ends 108 of latches 106 engage the undercut in the I.V. bag port before travel of the needle carrier bottoms out, to thereby firmly secure the I.V. bag to the end fitting 90 while establishing a sealed flow path from mixing chamber 6 via flow bore 26 and second needle 96 into the I.V. bag. The mixed pharmaceutical can now be transferred by forcing piston 30 into the mixing chamber; e.g. by operating rotator 44.

After the transfer of the pharmaceutical from the mixing chamber to the I.V. bag is complete, an operator grasps the free finger tabs 114 of latches 106 and pushes inwardly on them to pivot the inner ends 108 thereof outwardly, thereby releasing the I.V. bag port and enabling its withdrawal.

To prevent any seepage of pharmaceutical from the free end of second needle 96 after the withdrawal of the I.V. bag, which typically runs from the free needle end downwardly along the exterior of the needle, an absorbent disk 116 for absorbing any such liquid is preferably interposed between the needle carrier 94 and the end of the I.V. bag port when the latter is inserted into tubular passage 110. Upon the removal of the I.V. bag, the absorbent disk remains in place; that is, on top of the needle carrier (as seen in FIG. 1) and snugly surrounding the needle protruding therefrom.

This completes the preparation of the pharmaceutical and its delivery into the I.V. bag for subsequent administration to a patient. The mixing and delivery device 2 of the present invention is thereafter preferably immediately disposed of to prevent its reuse and possible contact with any residue of the components and/or the mixed pharmaceutical that may remain in the device or at the respective ports.

What is claimed is:

1. A method of preparing a pharmaceutical solution requiring a mixing of first and second liquid components of the pharmaceutical solution for its subsequent intravenous administration comprising the steps of providing syringe structure including a mixing chamber fluidly coupled to first and second ports which are normally sealed from the chamber, and a reciprocating piston in the chamber; furnishing first and second closed vials holding the respective components in their interiors; establishing flow communication which is sealed to a surrounding environment via the first port between the interior of the first vial and the chamber; flowing the first component into the chamber; repeating the establishing and flowing steps with the second vial holding the second component to thereby also mix the components and form the solution; thereafter resealing the first port from the mixing chamber; providing an I.V. bag and opening flow communication via the second port between the chamber and an interior of the bag; flowing the pharmaceutical solution from the chamber into an interior of the I.V. bag; and thereafter resealing the second port from the mixing chamber; whereby the solution is formed from the components and transferred into the I.V. bag while preventing contact with the components and the solution from the surrounding environment.

2. A method according to claim 1 wherein the step of providing the I.V. bag and opening flow communication comprises attaching the I.V. bag to the syringe structure, and including the step of removing the I.V. bag from the syringe structure after the step of resealing the second port.

3. A method according to claim 2 including the step of discarding the syringe structure to prevent its subsequent reuse after the removing step.

4. A method according to claim 1 wherein the ports include longitudinally movable needle cannulas, and wherein the steps of establishing and opening comprise moving the respective cannulas in a first longitudinal direction of the needle.

5. A method according to claim 2 including the step of absorbing solution remnants present at the port after the step of removing the I.V. bag.

6. A method according to claim 1 wherein the syringe structure includes a piston reciprocating along an axis of the chamber, and wherein the steps of flowing comprise rotating a member about the axis and translating rotary motion of the member into reciprocating motion of the piston to thereby facilitate flowing liquid components having a relatively high viscosity.

7. A method according to claim 6 including the step of interrupting the translating step when, during the rotating step, a torque applied to the member exceeds a predetermined threshold.

8. A method according to claim 1 wherein at least one of the components includes a compound for the treatment of cancer.

9. A method according to claim 8 wherein at least one of the components comprises a diluent.

10. A method according to claim 8 wherein the compound comprises a compound obtained from a yew tree.

11. A method according to claim 4 wherein the steps of resealing comprise moving the respective needles in a second longitudinal direction opposite to the first direction.

12. Apparatus for preparing a pharmaceutical solution requiring a mixing of first and second liquid components of the pharmaceutical solution for its subsequent intravenous administration, the apparatus comprising a syringe structure including a mixing chamber in fluid communication with spaced-apart first and second ports on the structure; a normally closed valve for each port in fluid communication with the mixing chamber and the respective ports; and a holder at each port for attaching containers to the syringe structure, each holder including a linearly reciprocable member operatively coupled to the associated valve for opening the valve in response to movement of the member in a first direction and closing of the valve in response to movement of the member in a second, opposite direction; whereby containers holding the pharmaceutical components can be sequentially connected to the first port for sequentially flowing the components into the chamber and mixing them therein, and a further container can be connected to the second port for flowing the solution from the chamber into the further container.

13. Apparatus according to claim 12 including a closure cup adapted to be placed over containers connected to the first port and detachably, sealingly secured to the syringe structure for sealing containers connected to the first port from a surrounding environment, the cup including means for imparting movement to the holder at the first port in the first and second directions.

14. Apparatus according to claim 12 wherein an interior of the containers is sealed from a surrounding environment, and wherein each holder includes a cannula having a free end for establishing fluid communication with the interior of the respective containers when connected to the respective holders.

15. Apparatus according to claim 14 wherein a portion of each cannula is operatively coupled to the associated valve for opening and closing the valve.

16. Apparatus according to claim 15 wherein the cannula portion comprises a closed cannula end and a lateral orifice from an interior of the cannula to an exterior thereof and located proximate the closed end.

17. Apparatus according to claim 16 wherein the closed end and the orifice are disposed on an interior portion of the syringe structure when the associated valves are in their open and closed positions.

18. Apparatus according to claim 17 wherein the valve comprises an elastomeric sleeve snugly engaging the portion of the cannula.

19. Apparatus according to claim 17 wherein each elastomeric sleeve is positioned and dimensioned so that movement of the associated cannula in the first direction disengages the cannula portion from the elastomeric sleeve to thereby establish fluid communication from the cannula interior and the chamber for enabling a liquid flow between the corresponding container and the chamber.

20. Apparatus according to claim 12 including means biasing the holder in the second direction into a position in which the valve is closed.

21. Apparatus according to claim 20 wherein the holder includes a needle cannula and the biasing means comprises a compression spring surrounding the cannula.

22. Apparatus according to claim 12 wherein the chamber is a cylindrical chamber having an end in fluid communication with the ports, and wherein the syringe structure includes a piston reciprocably disposed in the cylindrical chamber and means for manually reciprocating the piston.

23. Apparatus according to claim 22 wherein the manually reciprocating means comprises a rotator rotatable about an axis of the cylindrical chamber and a motion translator for converting rotary motion of the member into reciprocating linear motion of the piston to provide a mechanical advantage facilitating flowing liquids having a relatively high viscosity into and out of the chamber.

24. Apparatus according to claim 23 wherein the translator comprises a threaded connection between the rotator and the syringe structure which is concentric with the axis of the cylindrical chamber.

25. Apparatus according to claim 23 including a torque responsive coupling between the rotator and the piston preventing the translator from translating rotary motion into linear motion when a torque applied to the rotator exceeds a predetermined magnitude.

26. Apparatus according to claim 25 wherein the rotator is disposed concentrically within an opening in the piston and wherein the coupling comprises a resiliently compressed ring disposed between the rotator and the piston.

27. Apparatus for preparing and delivering to an I.V. bag a binary liquid cancer treatment pharmaceutical requiring a mixing of first and second liquid components furnished in first and second vials, each vial having an opening closed by a pierceable septum and leading to an interior of the vial, the apparatus comprising: a body including an elongated mixing chamber, a piston for drawing liquid into and expulsing liquid from the chamber, and first and second ports on an exterior of the body and in fluid communication with the chamber; a vial docking cage reciprocably mounted to the body at the first port and comprising a first member mounting a first needle cannula having a pointed free end, a closed end at an interior of the body, and a lateral orifice proximate the closed end and open to an interior of the cannula; first means biasing the first member away from the body; a connector adapted to releasably engage and position a vial on the first member so that the pointed free cannula end pierces the septum of the vial to establish flow communication between the vial interior and the cannula interior which is sealed from a surrounding environment; an elastomeric tubular first valve mounted in the body, in fluid communication with the chamber, surrounding and covering the orifice of the first needle cannula when the cage is relatively remote from the body and uncovering the orifice and thereby establishing fluid communication between the orifice and the chamber when the cage is proximate the body so that retraction of the piston in the chamber draws liquid from the vial interior via the first needle cannula, its orifice and the first valve into the chamber, and movement of the cage induced by the biasing means to the position remote from the body causes the first valve to cover the first orifice to prevent further fluid communication between the first needle cannula and the chamber; the second port including a needle carrier mounted to the body and movable towards and away from the body, the carrier including a holder for releasably holding the I.V. bag, a second needle cannula having a pointed free needle end for piercing the I.V. bag, a closed end at the interior of the body and a lateral second orifice proximate the closed end communicating with an interior of the second cannula, and second means biasing the carrier into an extended position away from the body; and an elastomeric tubular second valve mounted in the body, in fluid communication with the chamber, surrounding and covering the second orifice when the carrier is in its extended position, and uncovering the second orifice and thereby establishing fluid communication between the interior of the second cannula and the chamber when the carrier is in a retracted position proximate the body so that movement of the piston into the chamber flows the mixed pharmaceutical from the chamber via the second valve and the second cannula into the I.V. bag.

28. Apparatus according to claim 27 including means engaging the vial for moving the vial and therewith reciprocating the cage.

29. Apparatus according to claim 28 wherein the engaging means comprises a closed cup surrounding the vial and threadably connected with the body.

30. Apparatus according to claim 27 including a reciprocating thread connection operatively interposed between the body and the piston for reciprocating the piston in the chamber by rotating a member to provide a mechanical advantage and facilitate the flow of liquid between the ports and the chamber.

31. Apparatus according to claim 30 including a coupling operatively connected with the piston for preventing reciprocating motion of the piston when a torque applied to the member exceeds a predetermined magnitude.

32. Apparatus according to claim 27 wherein the connector includes jaws resiliently mounted on the first member for engaging the vial adjacent its opening.

33. Apparatus according to claim 32 including means locking the jaws in their vial engaging positions while the orifice of the first cannula is uncovered by the first valve.

34. Apparatus according to claim 27 wherein the I.V. bag includes a sealed tubular port pierceable by the free second cannula end, and wherein the second port includes at least one latch member shaped, positioned and mounted to engage a portion of the tubular port and releasably retain it to the carrier.

35. Apparatus according to claim 27 wherein the first and second biasing means each comprises a spring.

36. Apparatus according to claim 35 wherein spring forces exerted by the respective springs are greater than piercing forces required to be exerted against the free ends of the first and second cannulas for piercing the septums and the closed tubular port, respectively, so that the piercing occurs before the respective valves uncover the associated needle orifices.

37. Apparatus for delivering to an I.V. bag a liquid pharmaceutical made from mixed liquid components furnished in separate containers while precluding contact with components and the pharmaceutical, the apparatus comprising a body including a mixing chamber and first and second ports in liquid communication with the chamber; a reciprocating holder for alternatingly positioning first and second septum-sealed vials holding the respective components at the first port; a first needle cannula mounted on the holder for piercing the septum; a normally closed first valve between the first cannula and the chamber; and means operatively coupled with the first cannula and the first valve for opening the first valve in response to movement of the holder in a first direction and for closing the first valve in response to movement of the holder in a second direction;

the second port comprising a carrier movable between proximate and remote positions relative to the housing and adapted to releasably engage a sealed, pierceable port of the I.V. bag for receiving the pharmaceutical from the chamber, the carrier including a second needle cannula with a pointed end for piercing the tubular port; a normally closed second valve between the second cannula and the chamber; and means operatively coupled with the second cannula and the second valve for opening and closing the second valve in response to movements of the carrier between the proximate and remote positions; whereby the components are sequentially drawn into the chamber by attaching and detaching the first and second vials to and from the holder, moving the holder to establish and prevent fluid communication between the chamber and the first and second vials and operating the piston, and whereby the pharmaceutical is subsequently transferred to the I.V. bag after the carrier has at least been partially moved between the proximate and remote positions to uncover the orifice in the second cannula so that the mixed liquid pharmaceutical flows from the chamber into the I.V. bag.

* * * * *